(12) United States Patent
Nigam

(10) Patent No.: US 8,880,162 B2
(45) Date of Patent: Nov. 4, 2014

(54) DEVICE, METHOD, AND COMPUTER-READABLE STORAGE MEDIUM FOR DETECTING EVENTS IN CARDIAC SIGNALS

(75) Inventor: Indra B. Nigam, Tigard, OR (US)

(73) Assignee: BIOTRONIK CRM Patent AG (CH)

( * ) Notice: Subject to any disclaimer, the term of this patent is extended or adjusted under 35 U.S.C. 154(b) by 949 days.

(21) Appl. No.: 12/941,442

(22) Filed: Nov. 8, 2010

(65) Prior Publication Data

US 2011/0125043 A1 May 26, 2011

Related U.S. Application Data

(60) Provisional application No. 61/259,226, filed on Nov. 9, 2009.

(51) Int. Cl.
*A61B 5/04* (2006.01)
*A61B 5/0456* (2006.01)
*A61B 5/00* (2006.01)

(52) U.S. Cl.
CPC ........... *A61B 5/0456* (2013.01); *A61B 5/04012* (2013.01); *A61B 5/7221* (2013.01)
USPC ....................................................... 600/523

(58) Field of Classification Search
USPC ................................................ 600/508–518
See application file for complete search history.

(56) References Cited

U.S. PATENT DOCUMENTS 5,810,740 A * 9/1998 Paisner .......................... 600/515
2007/0219453 A1* 9/2007 Kremliovsky et al. ........ 600/509

* cited by examiner

*Primary Examiner* — Carl H Layno
*Assistant Examiner* — Erica Lee
(74) *Attorney, Agent, or Firm* — Craig A. Fieschko, Esq.; DeWitt Ross & Stevens S.C.

(57) ABSTRACT

The present disclosure generally relates to a method, a device, and a computer-readable storage medium for detecting heart beats from cardiac signals whose quality, expressed in terms of signal amplitude and signal-to-noise ratio, varies dynamically in time.

Hence, a method, a device, and a computer-readable storage medium for detecting electrical signals originating from a human or animal heart is proposed. The method includes the following steps:

a) identifying an initial indication of the event in at least one of the signal channels,
b) deciding whether or not the identified initial indication confirms the event depending on the quality of the signal channels in which initial indications are identified; and
c) determining a point-of-detection for the event depending on the quality of the signal channels and depending from the shape of the signal.

27 Claims, 7 Drawing Sheets

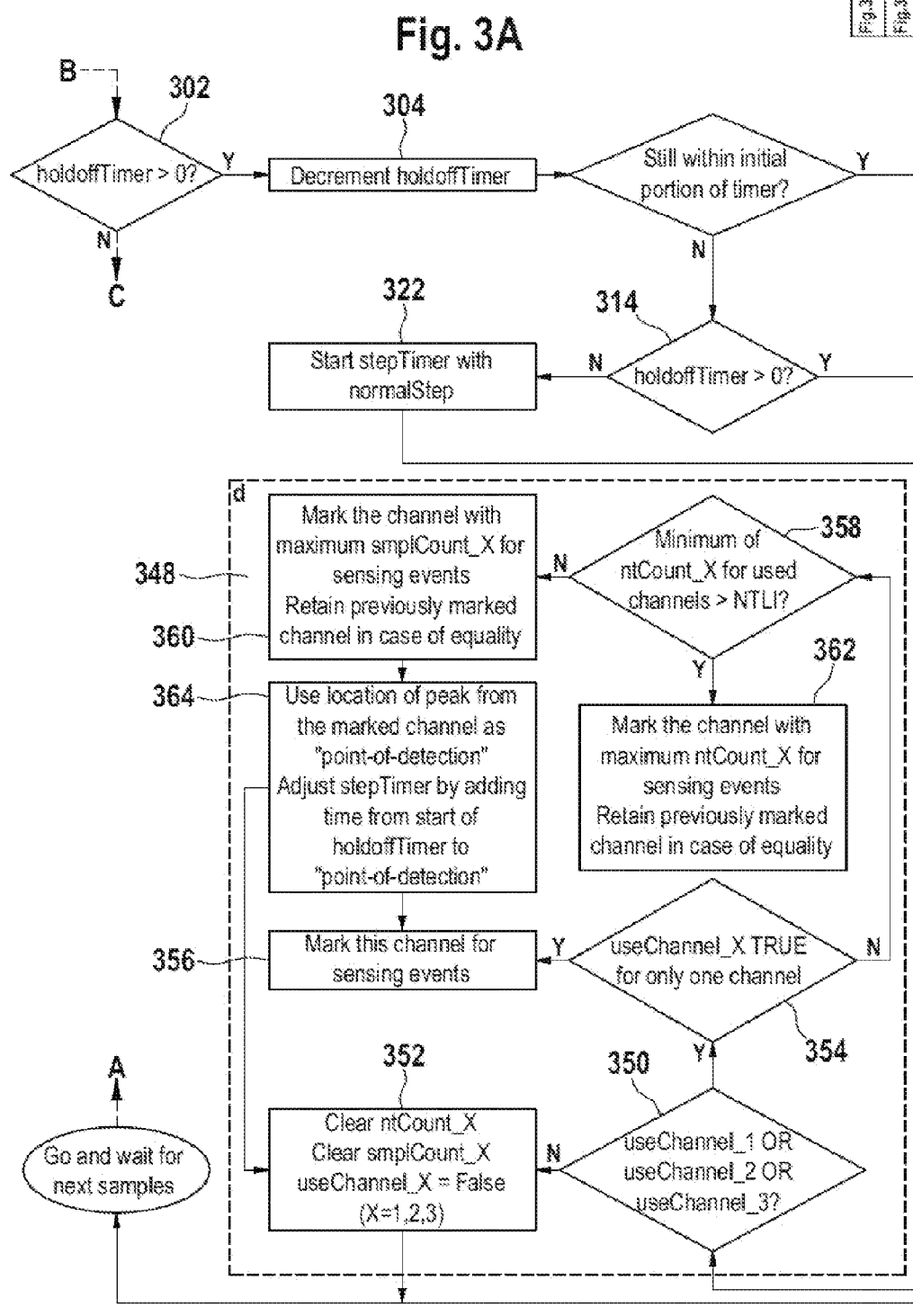

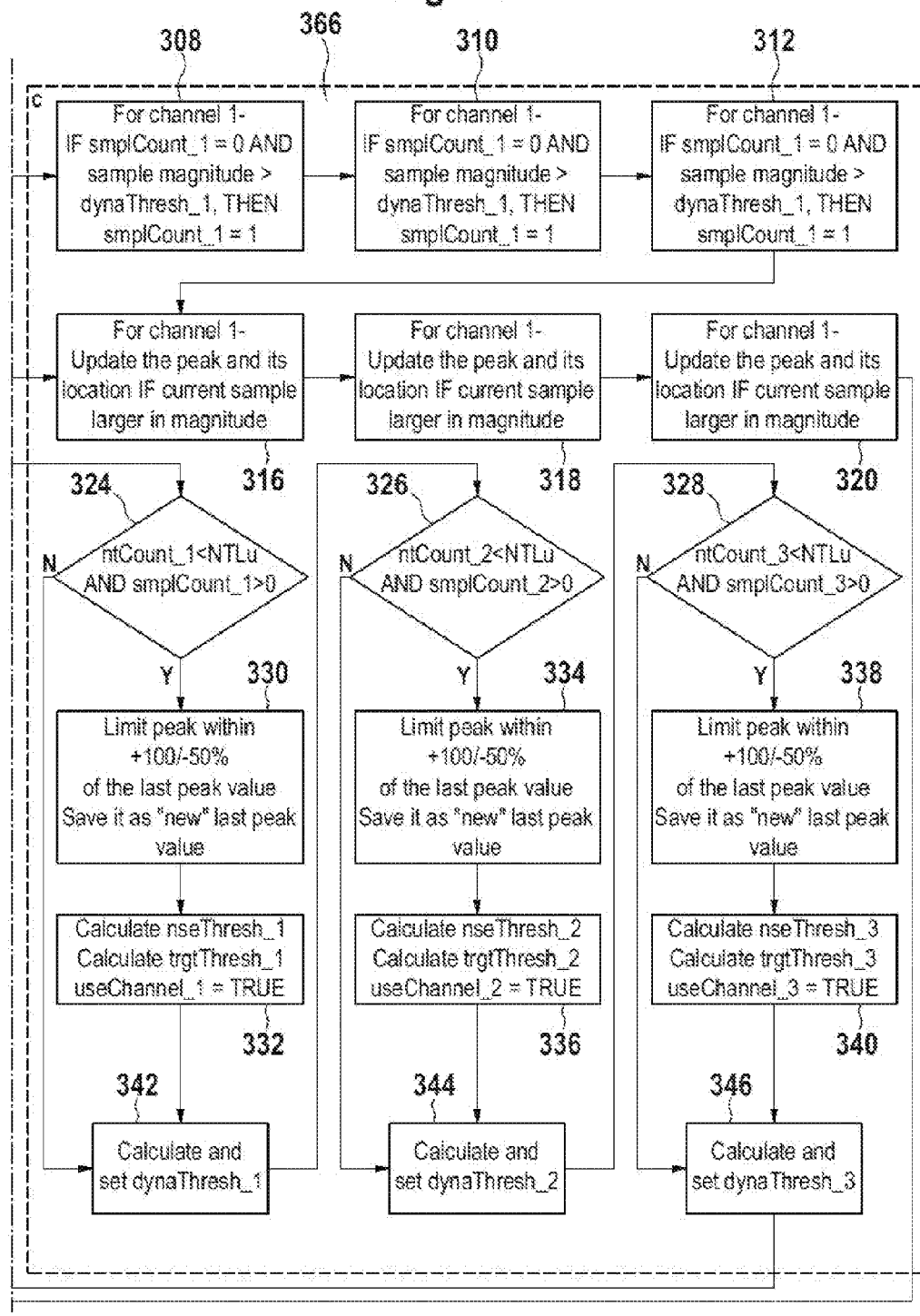

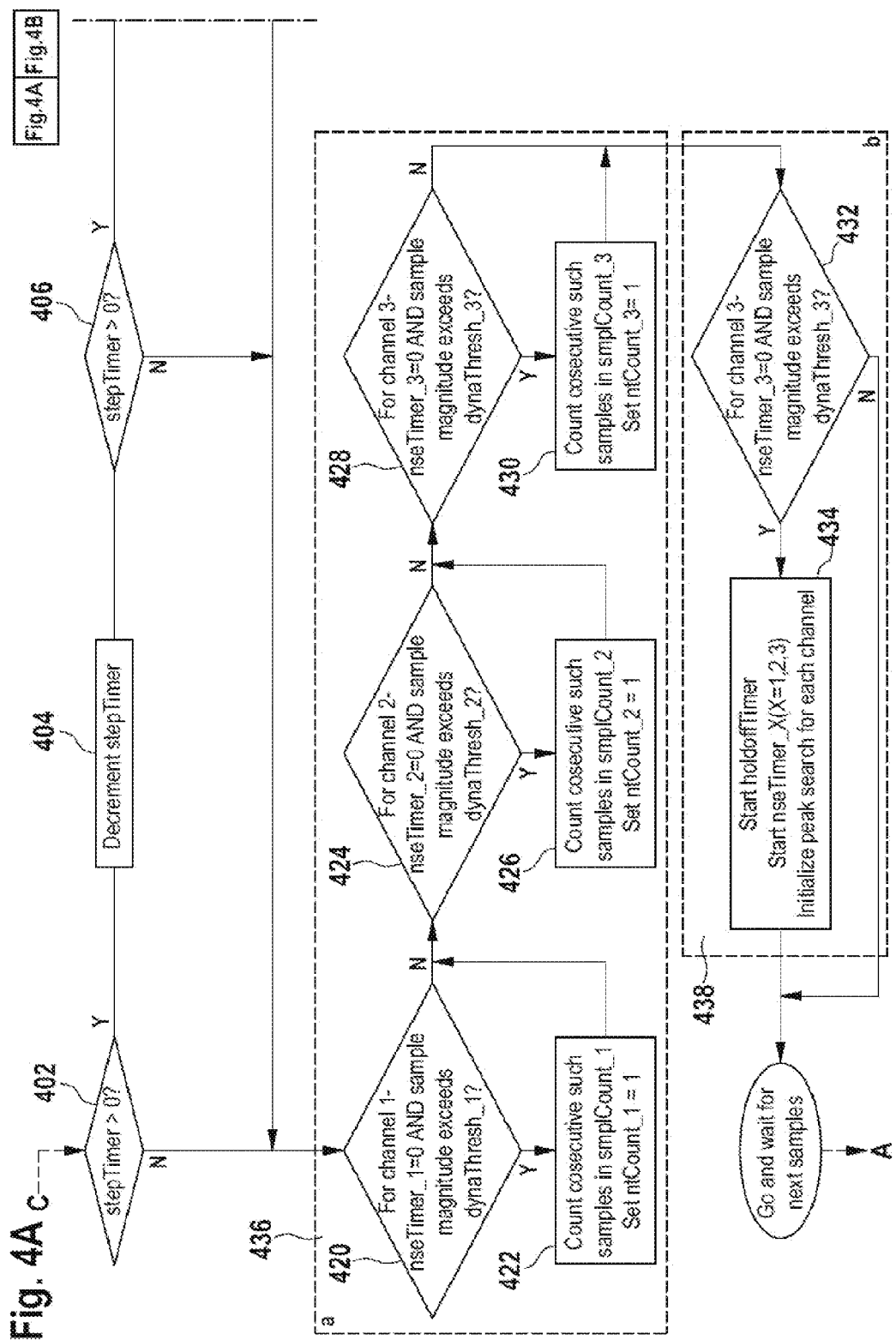

DEVICE, METHOD, AND COMPUTER-READABLE STORAGE MEDIUM FOR DETECTING EVENTS IN CARDIAC SIGNALS

RELATED APPLICATION

This patent application claims the benefit of U.S. Provisional Patent Application No. 61/259,226, filed on Nov. 9, 2009, which is hereby incorporated by reference in its entirety.

TECHNICAL FIELD

The present invention generally relates to a method, a device, and a computer-readable storage medium for detecting heart beats from cardiac signals whose quality, expressed in terms of signal amplitude and signal-to-noise ratio, varies dynamically in time. In addition, the present invention relates to detecting the heart beats from individual channels of a multi-channel cardiac signal.

BACKGROUND

There exist implantable monitoring devices that record and monitor electrical activity of the heart, which typically use at least two sensing channels originating from at least three sensing electrodes. While a multi-channel signal provides redundant capability for detecting heart beats, it is a challenge to select the most appropriate channel on a dynamic basis because the quality is expected to vary for the individual channels. The design must be suitable for incorporation in an implantable device.

SUMMARY

It is an object of the invention to provide a method, a device, and a computer-readable storage medium for detecting heart beats from a multi-channel cardiac signal by evaluating the quality of the signal and selecting the most appropriate channel on a dynamic basis. Using an automatic sense control scheme, the disclosed method analyzes the signal quality of the individual channels. Based on this analysis, the method accepts or discards detection results from the individual channels. To minimize any sensing-induced variability in the sensed heart intervals, the method associates the point of detection to the highest slope of the heart complex from the highest quality channel.

In one aspect of the present disclosure, a device is provided for example an implantable cardiac device, such as a pacemaker, a defibrillator, a cardioverter or a monitoring device, for detecting events like heart beats from cardiac signals of a multi-channel system. The device comprises sensors such as electrodes for detecting cardiac signals, a power supply, and processing, control, and storage means, including a processor (e.g., a CPU) configured to execute a method for detecting events like heart beats from cardiac signals, the method comprising the following steps:
(a) identifying an initial indication of the event in at least one of the signal channels,
(b) deciding whether or not the identified initial indication confirms the event depending on the quality of the signal channels in which initial indications are identified; and
(c) determining a point-of-detection depending on the quality of the signal channels and depending on the shape of the signal.

The method detects heart beats from a multi-channel cardiac signal that preferably includes at least two signal channels.

The method consists of three stages:
(i) Find an initial indication of a heart beat in the individual channels (initial-indication phase),
(ii) Assess the signal quality to decide whether or not the channel-specific indications confirm a heart beat (heart-beat-confirmation phase), and
(iii) Determine the point-of-detection to the location of the highest slope of the highest quality channel (synchronization phase).

In a preferred embodiment, the initial indications of a heart beat are multiple consecutive samples having magnitudes that exceed a settable detection threshold dynaThresh_X (where X=1, 2, 3, . . . , n denotes the channel number) while a noise timer nseTimer_X is inactive. The noise timers and the detection threshold levels are channel-specific. The accumulated count smplCount_X of such samples, when equal to a predetermined limit, to gives an initial indication of a heart beat.

In a preferred embodiment, the signal quality of individual channels is assessed by the number ntCount_X of times the noise timer is restarted, and by the number smplCount_X of consecutive-samples-exceeding-detection-threshold.

It is proposed that the noise timers for all channels are started following the initial indication of a heart beat. If not already expired, the noise timer is restarted each time the sample magnitude rises above the noise threshold nseThresh_X or the sample polarity changes while the magnitude remains above the noise threshold nseThresh_X.

It is further proposed that consecutive-samples-exceeding-detection-threshold are counted for all channels, summed and compared against a predetermined limit to give initial indication of a heart beat. The initial indication sets a detection holdoff timer and initialization of peak searches in the individual channels.

In a preferred embodiment, while the detection holdoff timer is not yet expired, searches for the largest magnitude sample in the individual channels are carried out. Also, any channel that lacked a sample exceeding the detection threshold during the initial indication phase is assigned a count of one if a sample-exceeding-detection-threshold condition is met during an initial interval of the holdoff timer.

In an alternative embodiment, the process of counting consecutive-samples-exceeding-detection-threshold continues during the initial portion of a holdoff timer interval. In this alternative mode, largest count of consecutive-samples-exceeding-detection-threshold is used in the heart-beat-confirmation phase.

In another embodiment, upon the expiry of the holdoff period, a target trgtThresh_X and a noise threshold nseThresh_X are calculated for those channels where at least one sample exceeded the detection threshold dynaThresh_X and which did not get excessive noise timer restarts; furthermore, only these channels are used in the heart-beat-confirmation phase and are marked as being "in use". In a preferred embodiment of the inventive method, the said target trgtThresh_X and a noise threshold nseThresh_X are calculated using the peak values of the signal in the channels. Finally, in another preferred embodiment, for all channels, the detection thresholds dynaThresh_X are calculated from the target thresholds trgtThresh_X.

In another embodiment of the inventive method, the most appropriate channel is determined using noise-restarts counts ntCount_X and consecutive-samples-exceeding-detection-threshold counts smplCount_X for channels that are "in use" in the heart-beat-confirmation phase.

In a preferred embodiment it is proposed to determine the most appropriate channel in the following manner:
(i) In case none of the channels is "in use" at this point, no event detection is confirmed.
(ii) In case a single channel is "in use" at this point, event detection from this channel is confirmed.
(iii) Otherwise, if the minimum of the noise-restarts counts ntCount_X exceeds a predetermined noise count limit NTL1, event detection from the channel with the lowest noise-restarts count ntCount_X is confirmed.
(iv) If the minimum value of the noise-restarts counts ntCount_X does not exceed the predetermined noise count limit NTL1, event detection from the channel with the largest consecutive-samples-exceeding-detection-threshold count smplCount_X is confirmed.

In a preferred embodiment it is proposed that the point-of-detection is determined to the location of the peak from the confirmed channel.

It is another object of the invention to provide a device for detecting events in cardiac signals comprising control and storage means, the device being arranged for executing a method for detecting events in cardiac signals, the method comprising the following steps:
(a) identifying an initial indication of the event in at least one of the signal channels,
(b) deciding whether or not the identified initial indication confirms the event depending on the quality of the signal channels in which initial indications are identified; and
(c) determining a point-of-detection for the event depending on the quality of the signal channels and depending on the shape of the signal.

In a preferred embodiment of the inventive device, the device comprises multiple sensing electrodes for providing at least two sensing channels.

The device may be an implantable cardiac device, such as a pacemaker, a defibrillator, a cardioverter or a monitoring device.

A further object of the invention is to provide a computer-readable storage medium storing program code for causing a data processing device to perform a method for detecting events in cardiac signals originating from at least two signal channels, the method comprising the steps of:
(a) identifying an initial indication of the event in at least one of the signal channels,
(b) deciding whether or not the identified initial indication confirms the event depending from the quality of the signal channels in which initial indications are identified; and
(c) determining a point-of-detection for the event depending from the quality of the signal channels and depending from the shape of the signal.

The invention may be implemented in software, in hardware, or as a mixed-mode solution. In the case of a hardware solution, the processor component of the device may comprise electrical circuitry as opposed to a CPU that executes a program code.

The method is suitable for implantable devices as well as for external devices, remote databases, expert systems, or the like for further evaluation. The method disclosed provides reliable and accurate heart beat detection. Incorporation of the method in implantable monitoring devices shall provide reliable heart beat intervals to other device features such as Atrial fibrillation (AF) detection.

The details of the invention can be understood from the following drawings and the corresponding text descriptions.

DESCRIPTION OF THE DRAWINGS

FIG. 3 is a flow chart illustrating steps of calculating the target trgtThresh_X and a noise threshold nseThresh_X and determining the most appropriate channel;

DETAILED DESCRIPTION

Figure 1:
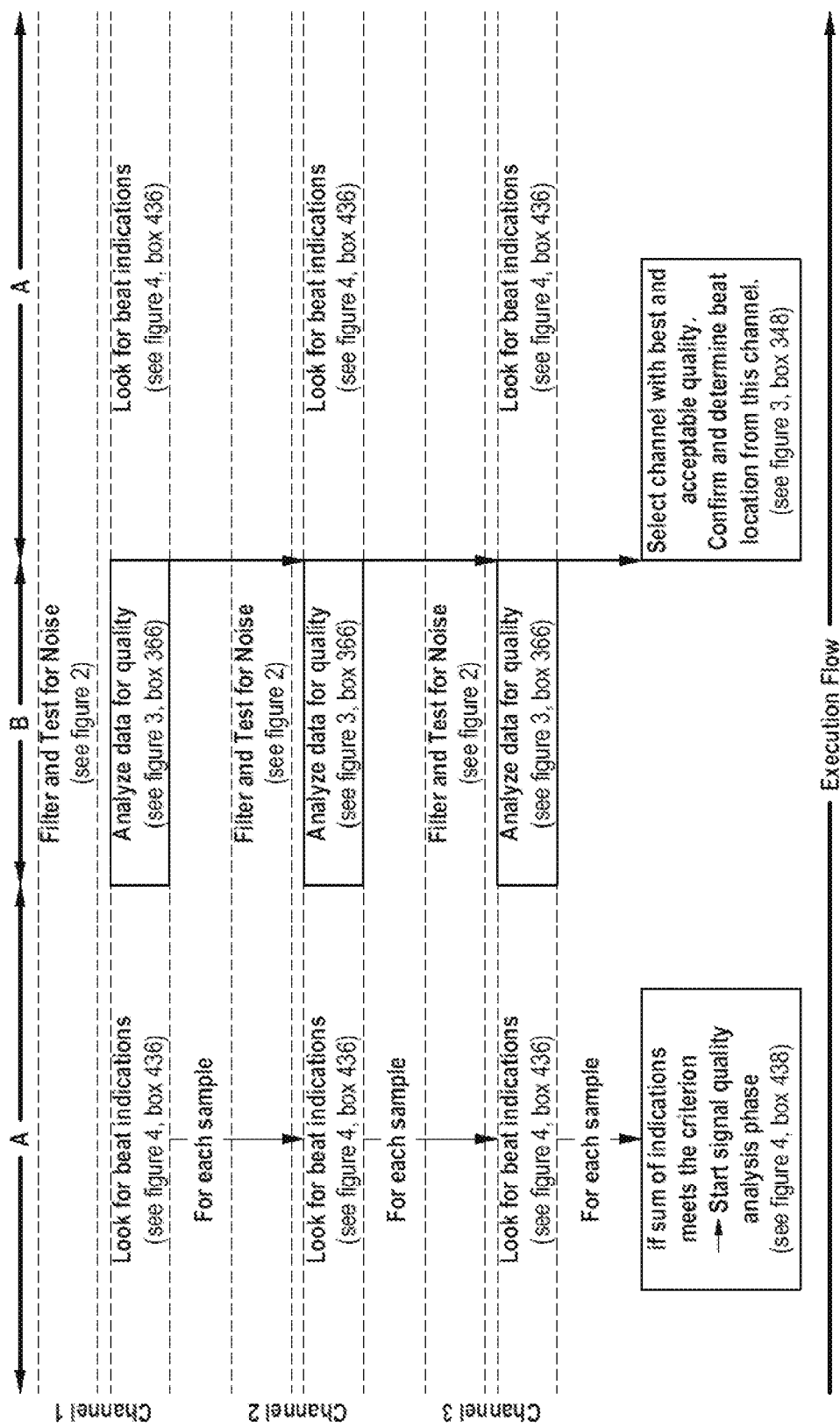
FIG. 1 is an illustration of main features of the invention in overview.
Figure 2:
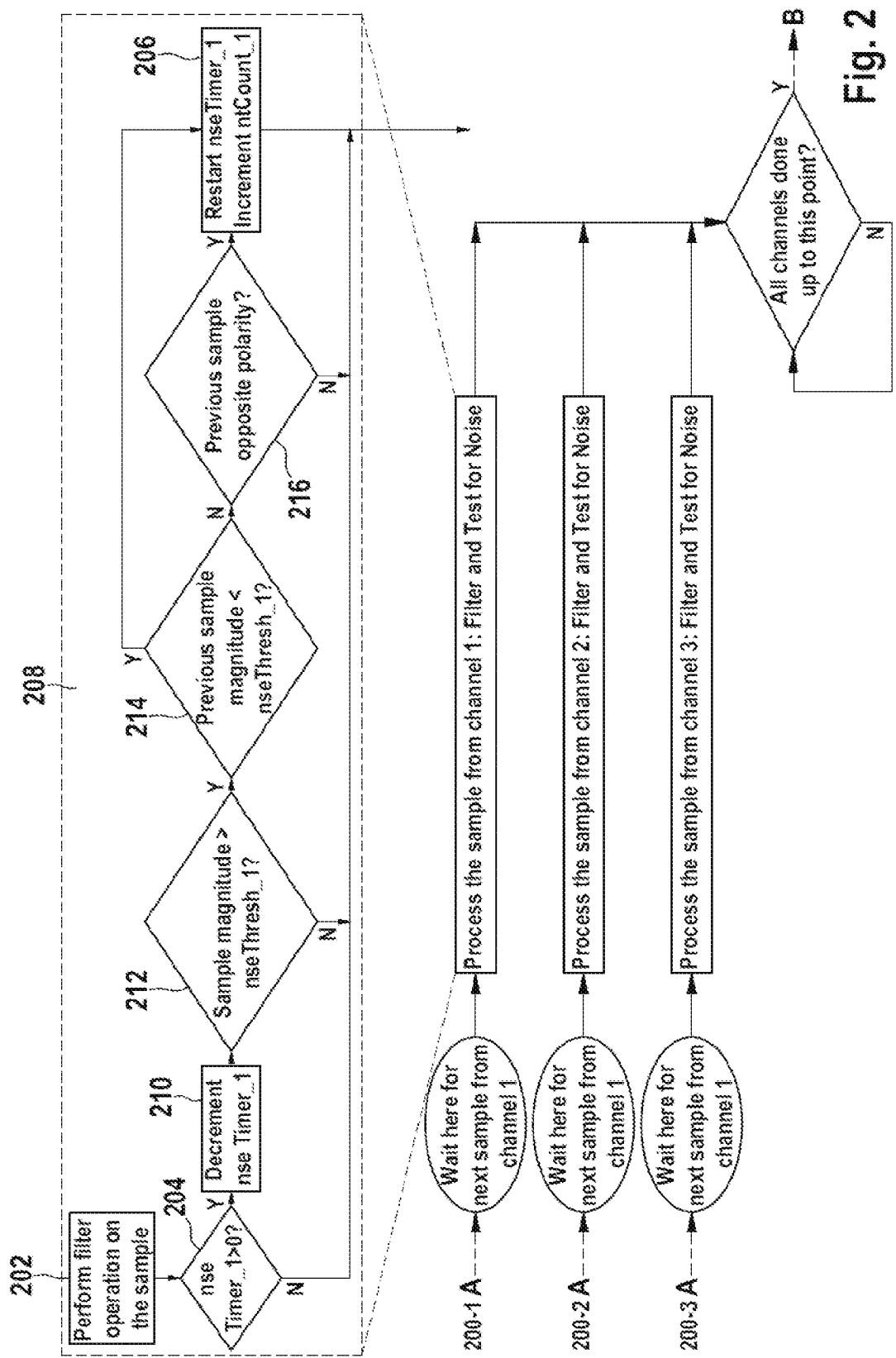
FIG. 2 is a flow chart illustrating steps of filtering and testing for noise in a preferred embodiment of the invention.
Figure 4B:
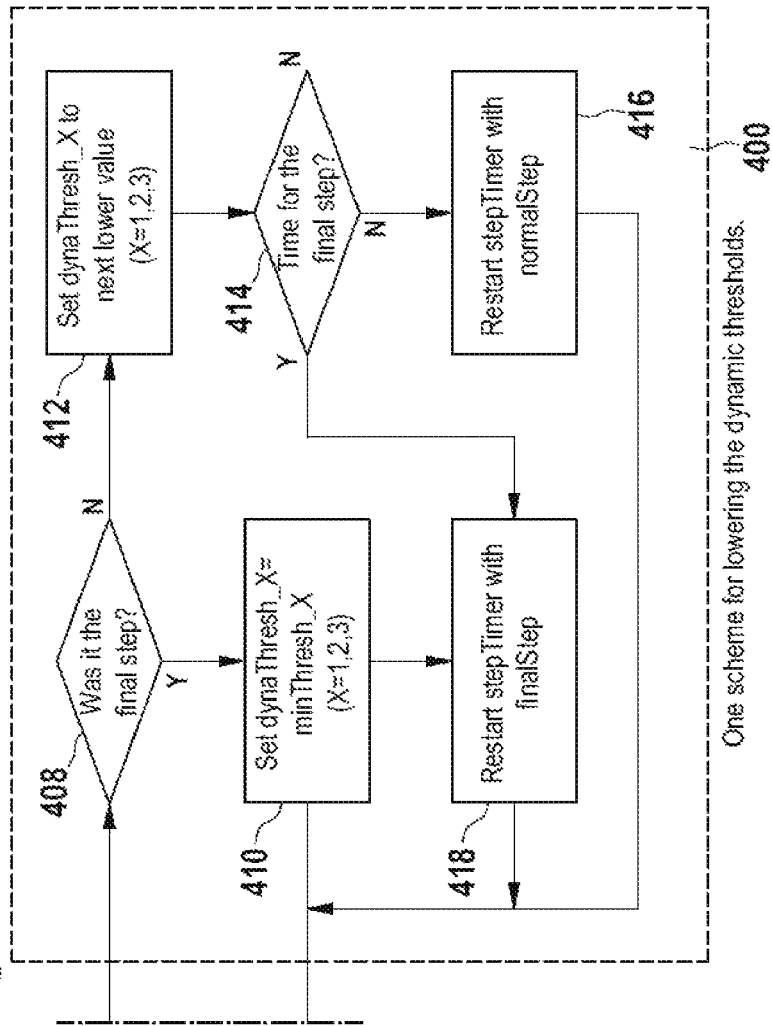
FIG. 4 is a flow chart illustrating steps of lowering the detection or dynamic threshold dynaThresh_X and of counting consecutive samples exceeding detection thresholds individually for each channel.

FIG. 1 presents an overview of the disclosed method, and FIGS. 2-4 address specific steps in greater detail. For incoming concurrent samples from each individual channel 200-1, 200-2, 200-3 (X=1,2,3 in the following) during a period A, the device looks for event indications (see FIG. 4, boxes 436 and 438). If the sum of indications in one channel meets a sample count limit, a signal quality analysis phase is started during a period B, and the respective channel is marked as being "in use" (see FIG. 3, box 366). As long as at least one channel is in use, the event is confirmed. For confirmation, the channel "in use" that has the best quality is selected and used for determining the point-of-detection (see FIG. 3, box 348).

In the following a special case is described, wherein the cardiac signal event is a heart beat. A flowchart depicted in FIGS. 1 to 4 illustrates a preferred embodiment having a 3-channel configuration.

Each of the channels 200-1, 200-2, 200-3 includes:
  a detection threshold, dynaThresh_X
  a sample counter, smplCount_X
  a target threshold, trgtThresh_X
  a pre-determined minimum threshold, minThresh_X
  a noise threshold, nseThresh_X
  a noise timer, nseTimer_X
  a noise-restarts counter, $ntCount_{\_X}$ The embodiment further includes:
  a detection holdoff timer having a pre-determined start value, holdoffTimer
  a pre-determined value for defining the initial portion of the detection holdoff timer
  a detection threshold reducing step timer, stepTimer
  a pre-determined value for the normal step, normalStep
  a pre-determined value for the final step, finalStep
  a pre-determined value for noise timers
  a pre-determined sample count limit for comparing the sum of smplCount_X
  a pre-determined excessive noise-restarts limit, NTLu
 a pre-determined noise count limit, NTL1

Calculation of noise and target thresholds, nseThresh_X and trgtThresh_X respectively, is not detailed because various different formulae can be used for this purpose; however, the calculations always utilize the measured peak values of the heart complex in the individual channels. Also, calculation of the initial dynamic thresholds is not detailed—it is directly based on the target threshold, and indirectly on the peak value used. Several different alternative formulae may be used.

The next sample from each of the channels 200-1, 200-2 and 200-3 is filtered in step 202 by a filter having appropriate pass-band characteristics. Depending upon whether or not the noise timer for the individual channel, nseTimer_X, has expired, as determined in step 204, the timer may be restarted and the noise restarts counter, ntCount_X, may be incremented in step 206. (See FIG. 2).

In detail, filtering and noise handling of incoming concurrent samples from each individual channel, as shown in box 208, comprises the following steps: Each incoming sample is first filtered in step 202. Then, in step 204, it is decided whether noise timer nseTimer_X has expired. If noise timer nseTimer_X has expired, filtering and noise handling of this sample is complete. If noise timer nseTimer_X has not yet expired, noise timer nseTimer_X is decremented in step 210. Subsequently, in step 212, it is decided, whether or not the sample magnitude exceeds the noise threshold nseThresh_X. If the sample magnitude does not exceed the noise threshold nseThresh_X, filtering and noise handling of this sample is complete. If the sample magnitude exceeds the noise threshold nseThresh_X, it is decided in step 214 whether or not the sample magnitude of the previous sample has exceeded the noise threshold nseThresh_X. If the noise threshold is esceeded, the noise timer nseThresh_X is restarted, the noise restarts counter, ntCount_X is incremented in step 206, and now filtering and noise handling of this sample is complete. If not, it is decided in step 216 whether or not the previous sample has opposite polarity. If the previous sample has opposite polarity, the noise timer nseThresh_X is restarted, the noise restarts counter, ntCount_X, is incremented in step 206, and now filtering and noise handling of this sample is complete. Also otherwise, filtering and noise handling of this sample is complete.

After completing filtering and noise handling of each set of incoming concurrent samples, in which a set consists of one sample from each individual channel, the process proceeds with step 302, where it is determined whether or not the holdoff timer, holdoffTimer, has expired.

As long as holdoffTimer has not expired yet, as determined in step 302, searches for a peak amplitude among the individual channels are carried out (see FIG. 3). However, the first action on the next sample is always filtering and noise handling as described above with respect to box 208. During the pre-determined initial portion of holdoffTimer, what is determined in step 306, if smplCount_X is zero for any channel, it can be set to 1 if the sample magnitude exceeds the detection threshold.

As an alternative to the procedure described in the preceding paragraph, during the predetermined initial portion of the holdoffTimer interval, the process of finding consecutive samples exceeding detection thresholds continues and, after the end of the initial portion, the Counter smplCount_X is given the largest sample count value obtained for the corresponding channel. This alternative mechanism is not shown in the flowchart.

Upon expiration of holdoffTimer, as determined in step 314, the nseThresh_X, trgtThresh_X and dynaThresh_X are calculated in steps 332, 336, 340, 342, 344 and 346 as described below in greater detail.

As long as the holdoffTimer has not expired, as determined in step 302, the holdoff timer is decremented in step 304, and in a subsequent step 306 it is determined whether the holdoff timer is still within the initial portion. In the case, the holdoff timer is still within the initial portion, in steps 308, 310 and 312 for each channel it is determined if the sample counter, smplCount_X, is equal to zero and if the sample magnitude is greater than the detection threshold, dynaThresh_X. If this condition is met, sample counter, smplCount_X, is set to 1. Subsequently, in steps 316, 318 and 320 the peak and its location are updated if the current sample is larger in magnitude. Then, the system awaits the next set of concurrent samples.

If it is determined in step 306 that the holdoff timer is no longer within the initial portion, it is determined in step 314 whether the holdoff timer after decrease in step 304 has expired. If not, steps 316, 318 and 320 are executed and the system waits for the next samples.

However, if in step 314 it is detected that the holdoff timer has expired, in step 322 the detection threshold reducing step timer, stepTimer, is started with normalStep. Subsequently, for each channel nseThresh_X, trgtThresh_X and dynaThresh_X are calculated. Calculation comprises the steps 324, 326 and 328, where it is determined whether the noise-restarts counter, ntCount_X is less than the pre-determined excessive noise-restarts limit, NTLu, and whether the sample counter, smplCount_X, is greater than zero. If this condition is met the process proceeds to steps 330, 332, 334, 336, 338 and 340, where the new peak is limited to remain within +100% to −50% of the preceding peak in the same channel, and the noise threshold, nseThresh_X, and the target threshold, trgtThresh_X, are calculated. (The flowchart in FIG. 3 shows delimitation of the new peak to remain within +100% to −50% of the preceding peak in the same channel. However, this delimitation is optional; a different range may be used.) Also, the respective channel status, useChannel_X, is set to TRUE, indicating the channel as being "in use." Irrespective of whether the condition in steps 324, 326 and 328 is met, in steps 342, 344 and 346 the detection threshold, dynaThresh_X, is calculated and set.

Upon expiration of holdoffTimer, as determined in step 314, the highest quality channel is marked for sensing the heart beat. And, the "point-of-detection" is determined to the location of the peak in the marked channel. This process uses ntCount_X and smplCount_X and is shown in the dotted box 348 of FIG. 3.

In step 350 it is determined whether there is at least one channel whose status, useChannel_X, is set to TRUE. If there is no such channel, in step 352 the noise-restarts counter, ntCount_X, and the sample counter, smplCount_X, are reset, and the status of all channels, useChannel_X, is set to FALSE. Then, for the system awaits the next samples. However, if there is at least one channel with useChannel_X=TRUE, it is decided in step 354 whether there is one or more such channels. If there is only one channel with useChannel_X=TRUE, in step 356 this channel is marked for sensing heart beats. If it is detected in step 354 that more than one channel has status TRUE, in steps 360 and 362 the channel with the greatest sample counter, smplCount_X, or the channel with the minimum noise-restarts counter, ntCount_X, is marked for sensing heart beats, where previously marked channels in case of equality are retained. This marking is done depending on the result of the test in step 358 where it is decided whether the minimum of noise-restarts counter, ntCount_X, for channels with status TRUE is greater than the pre-determined noise count limit, NTL1. Then, in step 364, the location of the peak from the marked channel is used as "point-of-detection," and the detection threshold reducing step timer, stepTimer, is adjusted by adding the time difference between the start of the detection holdoff timer and the "point-of-detection".

With reference to FIG. 4, if the detection holdoff timer, holdoffTimer, has expired, which is determined in step 302, the method continues as follows. Detection thresholds, dynaThresh_X, are lowered following a mechanism, for example, the one shown within the dotted box 400. While the embodiment shows one exemplary scheme 400 for lowering the detection or dynamic threshold dynaThresh_X, another mechanism may be used for the same purpose.

As long as the detection threshold reducing step timer, stepTimer, is greater than zero, which is determined in step 402, stepTimer is decremented in step 404. If, after the decrease, the detection threshold reducing step timer, stepTimer, is still greater than zero, which is detected in step 406, the detection thresholds, dynaThresh_X, are lowered. Lowering the detection thresholds, dynaThresh_X, comprises the step 408 of determining whether the present threshold reducing step is a final threshold reducing step. If yes, in step 410 the detection thresholds, dynaThresh_X, are set to the pre-determined minimum thresholds, minThresh_X. Otherwise, in step 412 the detection thresholds, dynaThresh_X, are set to the next lower value. In the subsequent steps 414, 416, 418 it is determined whether time for the final threshold reducing step is reached, and the detection threshold reducing step timer, stepTimer, is restarted with the pre-determined value for the normal step, normalStep, or with the pre-determined value for the final step, finalStep, depending on the decision in step 414.

Regardless of whether or not dynaThresh_X for the individual channels have reached the pre-determined minimum thresholds, search for initial indication of heart beat is made in each channel. In steps 420, 422, 424, 426, 428 and 430 consecutive samples with magnitudes exceeding detection thresholds are counted individually for each channel, smplCount_X. Search for initial indication of heart beat is not carried out in an individual channel if the associated noise timer, nseTimer_X, is still running, that is it contains a non-zero value.

If sum of smplCount_X reaches or exceeds the pre-determined sample count limit, which is determined in step 432, initial indication of a heart beat is declared. At this time, in step 434 holdoffTimer as well as nseTimer_X are started. Also, peak searches are initialized in individual channels.

Figure 5:
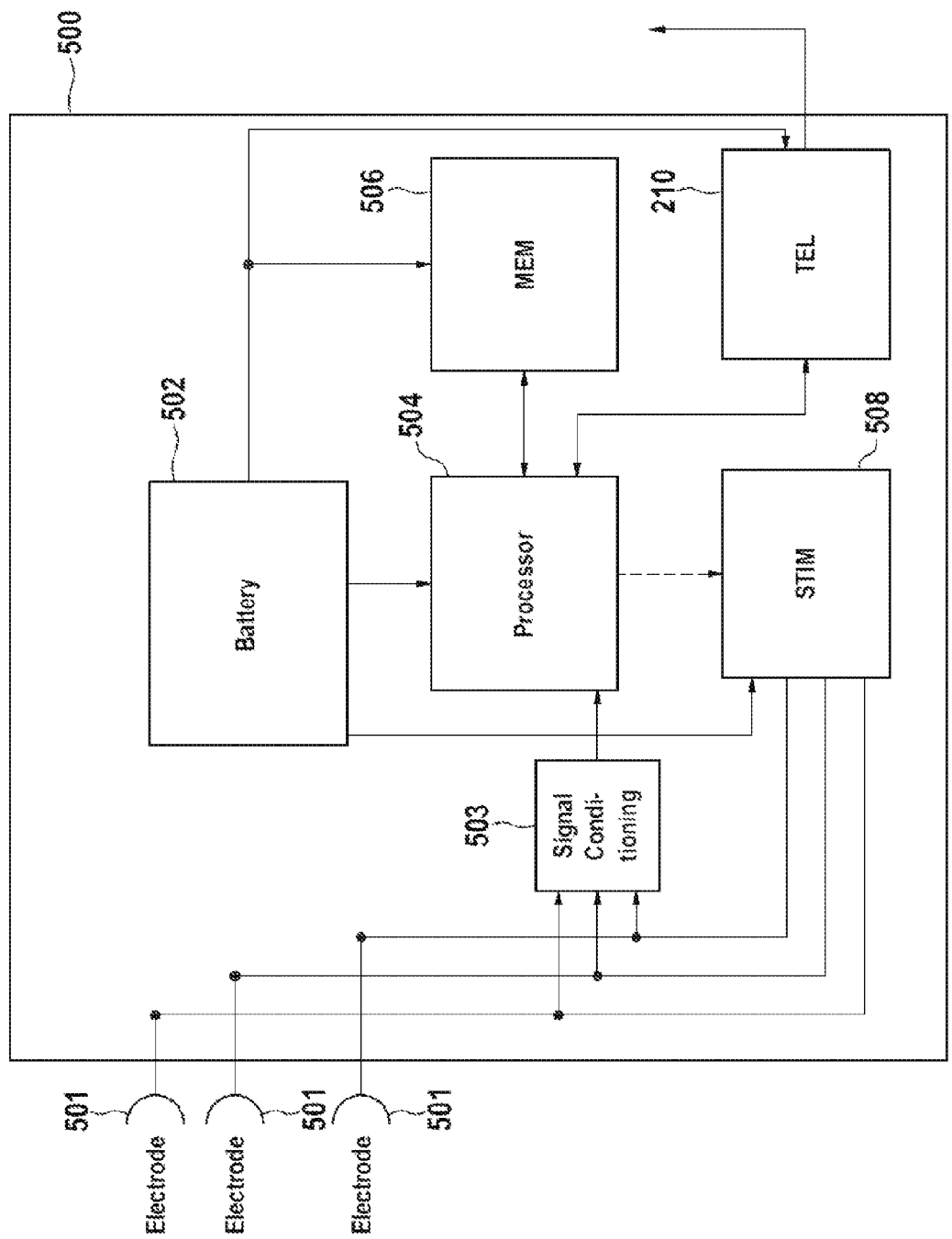
FIG. 5 is a block diagram of a multi-channel implantable cardiac device that may be configured to implement the disclosed method.

With reference to FIG. 5, a block diagram for a multi-channel implantable cardiac device (ICD) 500 is shown that may be configured to implement the method described above. ICD 500 is not the only such device, but is one example of such a device, in this case, one that entails the use of a combination of hardware and software. Electronic components of cardiac device 500 receive input signals from three cardiac sensing electrodes 501, each sensing electrode providing an individual sensing channel as input to the device, which nominally includes a power supply, preferably in the form of a battery 502, a signal conditioning unit 503 which, for example, may execute filter operation 202 shown in FIG. 2, and a processor 504, that may be used to execute instructions described in FIGS. 2-4, according to the method disclosed. Processor 504 preferably includes an on-board memory such as, for example, a random access type memory for storing variables (e.g., data and signals to be processed, counters, threshold values, and the like), or a cache memory for rapid data storage and retrieval. ICD 500 may optionally include a) a separate digital memory 506; b) a stimulation unit 508 that activates electrodes 501 to deliver therapeutic shocks, for example, if ICD 500 is configured as a cardiac pacemaker or defibrillator; and c) a telemetry unit 510 that communicates data to an external party, for example, if ICD is configured as a cardiac monitoring device.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A method for detecting events in cardiac signals originating from at least two signal channels in a cardiac medical device, the method comprising the following steps:
  a. identifying an initial indication of an event in signal samples from at least one of the signal channels,
  b. deciding whether or not the identified initial indication confirms the event depending on the quality of the signal channels in which initial indications are identified, each signal channel's quality being dependent on:
    (1) the number of consecutive samples in the signal channel exceeding a settable detection threshold, and
    (2) the number of times a noise timer for the signal channel is restarted, the noise timer being with the cardiac medical device, wherein the channel's noise timer is restarted if:
      i. a sample magnitude for the signal channel rises above a settable noise threshold, or
      ii. a sample polarity for the signal channel changes while the sample magnitude remains above the settable noise threshold; and
  c. determining a point-of-detection for the event depending on:
    (1) the quality of the signal channels, and
    (2) the shape of the signal.

2. The method according to claim 1, wherein step b comprises analyzing the quality of the signal channels, starting after a settable number of indications has been identified.

3. The method according to claim 1, wherein step b comprises, for confirmation of the event, selecting the channel that has the best quality.

4. The method according to claim 1, wherein for determining the point-of-detection, the channel having the best quality is selected.

5. The method according to claim 4, wherein the point-of-detection is determined to be the location of a peak from the selected channel.

6. The method according to claim 1, wherein the initial indication is identified depending on a number of consecutive samples having a magnitude that exceeds a settable detection threshold.

7. The method according to claim 6, wherein the initial indication is identified if an accumulated count of the consecutive samples having a magnitude that exceeds the settable detection threshold reaches a settable sample count limit.

8. The method according to claim 6, wherein, for determining the number of consecutive samples, such samples are considered which exceed the settable detection threshold while a noise timer is inactive.

9. The method according to claim 1, wherein the noise timer is started following the initial indication of an event.

10. The method according to claim 1, wherein at least one of the noise timer and the settable detection threshold are set to be channel-specific.

11. The method according to claim 1, wherein determining the point-of-detection depends on a slope of the signal.

12. The method according to claim 1, where after the initial indication of the event in at least one of the signal channels a detection holdoff timer is started, having an associated holdoff timer interval, and a search for a peak value is initialised in the signal channel.

13. The method according to claim 12, wherein, as long as the holdoff timer has not yet expired, the largest magnitude sample is searched in each of the channels.

14. The method according to claim 1, wherein, in step b for confirmation of the event, only such channels are used where a settable noise restart limit has not been reached.

15. The method according to claim 1, where step b comprises selecting the channel to be used for confirmation of the event depending on at least one of:
   a. a number of restarts of a noise counter in the channels, and
   b. a number of consecutive samples exceeding a settable threshold.

16. The method according to claim 1, wherein the event comprises heart beats.

17. A device for detecting events in cardiac signals sensed by electrodes configured to form at least two signal channels, the device comprising:
   a power supply;
   a signal conditioning unit; and
   a processor, in communication with the electrodes, via the signal conditioning unit, configured to receive the signal channels as input, and to analyze the cardiac signals to detect events by executing the steps of claim 1.

18. The device according to claim 17, further comprising electrodes for detecting the cardiac signals to form at least two signal channels.

19. The device according to claim 17, wherein the device is an implantable cardiac device (ICD), such as a pacemaker, a defibrillator, a cardiovertor or a monitoring device.

20. A non-transitory computer-readable storage medium storing program code for causing a processor to perform a method for detecting events in cardiac signals originating from at least two signal channels, the method comprising the steps of claim 1.

21. A method for detecting events in cardiac signals originating from at least two signal channels in a cardiac medical device, the method comprising the following steps:
   a. identifying an initial indication of an event in at least one of the signal channels,
   b. starting a detection holdoff timer, the detection holdoff timer being within the cardiac medical device, the detection holdoff timer having an associated holdoff timer interval during which the signal channels are searched for peak values, and wherein the holdoff timer interval comprises an initial portion in which a sample counter of a channel is incremented if a sample exceeds a settable detection threshold of the channel;
   c. deciding whether or not the identified initial indication confirms the event depending on the quality of the signal channels in which initial indications are identified; and
   d. determining a point-of-detection for the event depending on:
     (1) the quality of the signal channels, and
     (2) the shape of the signal.

22. The method according to claim 21, wherein, during the initial portion, counting of consecutive samples exceeding the settable detection threshold is continued.

23. A method for detecting events in cardiac signals originating from at least two signal channels in a cardiac medical device, the method comprising the following steps:
   a. identifying an initial indication of an event in at least one of the signal channels,
   b. starting a detection holdoff timer, the detection holdoff timer being within the cardiac medical device, the detection holdoff timer having an associated holdoff timer interval during which the signal channels are searched for peak values, and wherein, upon expiration of the holdoff timer interval, target thresholds and noise thresholds are calculated and set for channels where at least one signal sample has exceeded a settable threshold;
   c. deciding whether or not the identified initial indication confirms the event depending on the quality of the signal channels in which initial indications are identified; and
   d. determining a point-of-detection for the event depending on:
     (1) the quality of the signal channels, and
     (2) the shape of the signal.

24. The method according to claim 23, wherein the target thresholds and the noise thresholds are calculated using peak values of the signal in the respective channel.

25. The method according to claim 23, where the settable threshold for each channel for which target thresholds and noise thresholds are calculated is calculated from the target thresholds of the respective channel.

26. The method according to claim 23, wherein the target thresholds and the noise thresholds are calculated only for such channels where a settable noise restart limit has not been reached.

27. A method for detecting events in cardiac signals originating from at least two signal channels in a cardiac medical device, the method comprising the following steps:
   a. identifying an initial indication of an event in at least one of the signal channels,
   b. deciding whether or not the identified initial indication confirms the event depending on the quality of the signal channels in which initial indications are identified, wherein the signal channel to be used to confirm the event depends on at least one of:
     (1) a number of restarts of a noise counter in the channels, the noise counter being within the cardiac medical device, and
     (2) a number of consecutive samples exceeding a settable threshold, and the channel to be used for confirmation of the event is selected according to the following criteria:
       i. if there is no channel for which the number of restarts of the noise counter remains beneath a noise restart limit and the number of consecutive samples exceeding the settable threshold is greater than zero, then no detection is confirmed;
       ii. if there is only one channel for which the number of restarts of the noise counter remains beneath the noise restart limit and the number of consecutive samples exceeding the settable threshold is greater than zero, then detection from this channel is confirmed;
       iii. if a minimum value of a set of noise-restarts counts exceeds a settable noise count limit, then detection from the channel having the minimum value is confirmed;
       iv. if the minimum value of the set of noise-restarts counts does not exceed the noise count limit, then detection from the channel having the largest number of consecutive samples exceeding the settable threshold is confirmed;
   c. determining a point-of-detection for the event depending on:
     (1) the quality of the signal-channels, and
     (2) the shape of the signal.

\* \* \* \* \*